US008211181B2

(12) United States Patent
Walker (10) Patent No.: US 8,211,181 B2
(45) Date of Patent: Jul. 3, 2012

(54) SURFACE GUIDED KNEE REPLACEMENT

(75) Inventor: Peter Walker, New York, NY (US)

(73) Assignee: New York University, New York, NY (US)

( * ) Notice: Subject to any disclaimer, the term of this patent is extended or adjusted under 35 U.S.C. 154(b) by 875 days.

(21) Appl. No.: 11/304,107

(22) Filed: Dec. 14, 2005

(65) Prior Publication Data

US 2007/0135926 A1     Jun. 14, 2007

(51) Int. Cl.
*A61F 2/38* (2006.01)
(52) U.S. Cl. .................................... 623/20.21
(58) Field of Classification Search ..... 623/20.14–20.36
See application file for complete search history.

(56) References Cited

U.S. PATENT DOCUMENTS

| | | | | | |
|---|---|---|---|---|---|
| 4,224,697 | A | * | 9/1980 | Murray et al. | 623/20.25 |
| 4,538,305 | A | * | 9/1985 | Engelbrecht et al. | 623/20.25 |
| 4,634,444 | A | * | 1/1987 | Noiles | 623/20.27 |
| 4,790,853 | A | * | 12/1988 | Engelbrecht et al. | 623/20.25 |
| 4,959,071 | A | * | 9/1990 | Brown et al. | 623/20.27 |
| 5,139,521 | A | * | 8/1992 | Schelhas | 623/20.25 |
| 5,203,807 | A | * | 4/1993 | Evans et al. | 623/20.31 |
| 5,314,481 | A | * | 5/1994 | Bianco | 623/20.25 |
| 5,330,533 | A | * | 7/1994 | Walker | 623/20.31 |
| 5,413,607 | A | * | 5/1995 | Engelbrecht et al. | 623/20.24 |
| 5,427,586 | A | * | 6/1995 | Schelhas | 623/20.35 |
| 5,702,460 | A | * | 12/1997 | Carls et al. | 606/79 |
| 5,702,466 | A | * | 12/1997 | Pappas et al. | 623/20.29 |
| 5,800,552 | A | * | 9/1998 | Forte | 623/20.27 |
| 5,824,102 | A | * | 10/1998 | Buscayret | 623/20.21 |
| 5,871,539 | A | * | 2/1999 | Pappas | 623/20.31 |
| 5,871,546 | A | * | 2/1999 | Colleran et al. | 623/20.28 |
| 5,879,392 | A | * | 3/1999 | McMinn | 623/20.28 |
| 6,013,103 | A | * | 1/2000 | Kaufman et al. | 623/20.15 |
| 6,019,794 | A | * | 2/2000 | Walker | 623/20.22 |
| 6,039,764 | A | * | 3/2000 | Pottenger et al. | 623/20.32 |
| 6,074,424 | A | * | 6/2000 | Perrone et al. | 623/20.3 |
| 6,074,425 | A | * | 6/2000 | Pappas | 623/18.11 |
| 6,080,195 | A | * | 6/2000 | Colleran et al. | 623/20.32 |

(Continued)

OTHER PUBLICATIONS

Raymond P. Robinson, "The Early Innovators of Today's Resurfacing Condylar Kness", Arthroplasty, vol. 20, Suppl 1, 2005.

*Primary Examiner* — Alvin J. Stewart
(74) *Attorney, Agent, or Firm* — Kelley Drye & Warren LLP (57) ABSTRACT

An artificial knee joint that includes a femoral component with a specially shaped bearing surface and a tibial component, whose surface interacts with the femoral surfaces. The interaction provides for the required motion and stability characteristics. The interaction between the femoral and tibial surfaces is such that as the knee is flexed to maximum, the femoral component moves posteriorly on the tibial surface, by an amount similar to that in the anatomic knee. This is accomplished primarily by the depth and width of the femoral trochlea diminishing as the femoral component is flexed from zero to maximum, together with a ramp on the center of the tibial surface. The opposite motion, roll forward of the femur from a fully flexed to a more extended position, is accomplished by varying the outward radii of the lateral and medial femoral bearing surfaces, together with a ramp on the postero-lateral and postero-medial regions of the tibial surfaces. A variation of this is to generate a tibial surface which provides for a progressive internal rotation of the tibia as flexion proceeds.

12 Claims, 9 Drawing Sheets

U.S. PATENT DOCUMENTS

| | | | |
|---|---|---|---|
| 6,117,175 A * | 9/2000 | Bosredon | 623/20.15 |
| 6,123,729 A * | 9/2000 | Insall et al. | 623/20.31 |
| 6,126,693 A * | 10/2000 | O'Neil et al. | 623/20.32 |
| 6,143,034 A * | 11/2000 | Burrows | 623/20.29 |
| 6,152,960 A * | 11/2000 | Pappas | 623/20.31 |
| 6,165,222 A * | 12/2000 | Hoeppner et al. | 623/20.15 |
| 6,165,223 A * | 12/2000 | Metzger et al. | 623/20.27 |
| 6,203,576 B1 * | 3/2001 | Afriat et al. | 623/20.27 |
| 6,206,926 B1 * | 3/2001 | Pappas | 623/20.27 |
| 6,217,619 B1 * | 4/2001 | Keller | 623/20.34 |
| 6,235,060 B1 | 5/2001 | Kubein-Meesenburg et al. | |
| 6,264,696 B1 * | 7/2001 | Reigner et al. | 623/20.24 |
| 6,284,001 B1 * | 9/2001 | Knapp | 623/21.14 |
| 6,296,666 B1 * | 10/2001 | Gardner | 623/20.29 |
| 6,299,645 B1 | 10/2001 | Ogden | |
| 6,319,283 B1 * | 11/2001 | Insall et al. | 623/20.33 |
| 6,325,828 B1 | 12/2001 | Dennis et al. | |
| 6,387,131 B1 * | 5/2002 | Miehlke et al. | 623/20.15 |
| 6,406,497 B2 | 6/2002 | Takei | |
| 6,413,279 B1 * | 7/2002 | Metzger et al. | 623/20.29 |
| 6,416,552 B1 * | 7/2002 | Hoeppner et al. | 623/20.15 |
| 6,443,991 B1 * | 9/2002 | Running | 623/20.27 |
| 6,458,160 B2 * | 10/2002 | Biegun et al. | 623/20.27 |
| 6,475,241 B2 * | 11/2002 | Pappas | 623/20.29 |
| 6,485,519 B2 * | 11/2002 | Meyers et al. | 623/20.24 |
| 6,488,711 B1 * | 12/2002 | Grafinger | 623/20.24 |
| 6,527,807 B1 * | 3/2003 | O'Neil et al. | 623/20.15 |
| 6,540,786 B2 * | 4/2003 | Chibrac et al. | 623/18.11 |
| 6,589,283 B1 | 7/2003 | Metzger et al. | |
| 6,616,696 B1 * | 9/2003 | Merchant | 623/20.18 |
| 6,699,291 B1 * | 3/2004 | Augoyard et al. | 623/20.27 |
| 6,730,128 B2 * | 5/2004 | Burstein | 623/20.27 |
| 6,755,864 B1 * | 6/2004 | Brack et al. | 623/20.29 |
| 6,764,516 B2 * | 7/2004 | Pappas | 623/20.29 |
| 6,770,097 B2 * | 8/2004 | Leclercq | 623/20.15 |
| 6,773,461 B2 * | 8/2004 | Meyers et al. | 623/20.24 |
| 6,827,739 B2 * | 12/2004 | Griner et al. | 623/16.11 |
| 6,846,329 B2 * | 1/2005 | McMinn | 623/20.14 |
| 6,887,276 B2 * | 5/2005 | Gerbec et al. | 623/18.11 |
| 6,893,467 B1 * | 5/2005 | Bercovy | 623/20.14 |
| 6,902,582 B2 | 6/2005 | Kubein-Meesenburg et al. | |
| 6,962,607 B2 * | 11/2005 | Gundlapalli et al. | 623/22.29 |
| 6,972,039 B2 * | 12/2005 | Metzger et al. | 623/20.29 |
| 6,984,249 B2 * | 1/2006 | Keller | 623/20.24 |
| 6,986,791 B1 * | 1/2006 | Metzger | 623/20.24 |
| 7,025,788 B2 * | 4/2006 | Metzger et al. | 623/20.15 |
| 7,105,026 B2 * | 9/2006 | Johnson et al. | 623/20.14 |
| 7,150,761 B2 * | 12/2006 | Justin et al. | 623/20.14 |
| 7,232,465 B2 * | 6/2007 | Keller | 623/20.24 |
| 7,258,701 B2 * | 8/2007 | Aram et al. | 623/20.15 |
| 7,264,635 B2 | 9/2007 | Suguro et al. | |
| 7,297,164 B2 * | 11/2007 | Johnson et al. | 623/20.14 |
| 7,303,586 B2 * | 12/2007 | Keller | 623/20.29 |
| 7,309,362 B2 * | 12/2007 | Yasuda et al. | 623/20.31 |
| 7,326,252 B2 * | 2/2008 | Otto et al. | 623/20.15 |
| 7,351,263 B2 * | 4/2008 | Afriat | 623/20.27 |
| 7,354,454 B2 * | 4/2008 | Stack et al. | 623/23.65 |
| 7,364,590 B2 * | 4/2008 | Siebel | 623/20.35 |
| 7,413,577 B1 * | 8/2008 | Servidio | 623/20.14 |
| 7,465,320 B1 * | 12/2008 | Kito et al. | 623/20.27 |
| 7,497,874 B1 * | 3/2009 | Metzger et al. | 623/20.15 |
| 7,572,292 B2 * | 8/2009 | Crabtree et al. | 623/20.24 |
| 7,591,855 B2 * | 9/2009 | Keller | 623/20.24 |
| 7,615,081 B2 * | 11/2009 | Justin et al. | 623/20.14 |
| 7,658,767 B2 * | 2/2010 | Wyss | 623/20.29 |
| 2001/0003803 A1 * | 6/2001 | Leclercq | 623/20.29 |
| 2001/0018615 A1 * | 8/2001 | Biegun et al. | 623/20.35 |
| 2001/0021877 A1 * | 9/2001 | Biegun et al. | 623/20.28 |
| 2001/0034554 A1 * | 10/2001 | Pappas | 623/20.29 |
| 2001/0034555 A1 * | 10/2001 | Pappas | 623/20.29 |
| 2002/0010512 A1 * | 1/2002 | Takei | 623/20.31 |
| 2002/0022889 A1 * | 2/2002 | Chibrac et al. | 623/18.11 |
| 2002/0045947 A1 * | 4/2002 | Biegun et al. | 623/20.35 |
| 2002/0058997 A1 * | 5/2002 | O'Connor et al. | 623/20.32 |
| 2002/0120340 A1 * | 8/2002 | Metzger et al. | 623/20.15 |
| 2002/0156535 A1 * | 10/2002 | Pappas | 623/20.29 |
| 2003/0009228 A1 * | 1/2003 | Meyers et al. | 623/20.24 |
| 2003/0009229 A1 * | 1/2003 | Pappas | 623/20.27 |
| 2003/0009230 A1 * | 1/2003 | Gundlapalli et al. | 623/20.28 |
| 2003/0009231 A1 * | 1/2003 | Gundlapalli et al. | 623/20.29 |
| 2003/0163201 A1 * | 8/2003 | McMinn | 623/20.29 |
| 2003/0171815 A1 * | 9/2003 | Kana et al. | 623/20.15 |
| 2003/0208276 A1 * | 11/2003 | Berelsman et al. | 623/20.11 |
| 2004/0006393 A1 * | 1/2004 | Burkinshaw | 623/20.3 |
| 2004/0039450 A1 * | 2/2004 | Griner et al. | 623/20.31 |
| 2004/0054416 A1 * | 3/2004 | Wyss et al. | 623/20.27 |
| 2004/0068322 A1 * | 4/2004 | Ferree | 623/23.39 |
| 2004/0083003 A1 * | 4/2004 | Wasielewski | 623/20.21 |
| 2004/0102851 A1 * | 5/2004 | Saladino | 623/20.15 |
| 2004/0102852 A1 * | 5/2004 | Johnson et al. | 623/20.15 |
| 2004/0143339 A1 | 7/2004 | Axelson et al. | |
| 2004/0162620 A1 * | 8/2004 | Wyss | 623/20.27 |
| 2004/0186582 A1 | 9/2004 | Yasuda et al. | |
| 2004/0220676 A1 * | 11/2004 | Keller | 623/20.31 |
| 2004/0225368 A1 * | 11/2004 | Plumet et al. | 623/20.15 |
| 2004/0243244 A1 | 12/2004 | Otto et al. | |
| 2005/0055102 A1 * | 3/2005 | Tornier et al. | 623/20.32 |
| 2005/0102032 A1 * | 5/2005 | Beynnon et al. | 623/20.35 |
| 2005/0107883 A1 * | 5/2005 | Goodfried et al. | 623/20.15 |
| 2005/0154472 A1 * | 7/2005 | Afriat | 623/20.29 |
| 2005/0209701 A1 | 9/2005 | Suguro et al. | |
| 2006/0142867 A1 * | 6/2006 | Metzger et al. | 623/20.15 |
| 2006/0265078 A1 * | 11/2006 | McMinn | 623/20.14 |
| 2006/0265080 A1 * | 11/2006 | McMinn | 623/20.27 |
| 2006/0287733 A1 * | 12/2006 | Bonutti | 623/20.3 |
| 2007/0043444 A1 * | 2/2007 | Lester | 623/20.15 |
| 2008/0021566 A1 * | 1/2008 | Peters et al. | 623/20.16 |
| 2008/0058945 A1 * | 3/2008 | Hajaj et al. | 623/20.14 |
| 2008/0140212 A1 * | 6/2008 | Metzger et al. | 623/20.31 |
| 2009/0005875 A1 * | 1/2009 | Koenemann | 623/20.35 |
| 2009/0043396 A1 | 2/2009 | Komistek | |
| 2009/0204221 A1 * | 8/2009 | Walker | 623/20.27 |
| 2009/0265011 A1 * | 10/2009 | Mandell | 623/20.15 |
| 2009/0299482 A1 * | 12/2009 | Metzger et al. | 623/20.29 |
| 2009/0319047 A1 * | 12/2009 | Walker | 623/20.15 |
| 2009/0319048 A1 * | 12/2009 | Shah et al. | 623/20.29 |
| 2009/0326667 A1 * | 12/2009 | Williams et al. | 623/20.31 |
| 2010/0174378 A1 * | 7/2010 | Metzger et al. | 623/20.28 |
| 2010/0191341 A1 * | 7/2010 | Byrd | 623/20.3 |

\* cited by examiner

SURFACE GUIDED KNEE REPLACEMENT

FIELD OF THE INVENTION

The present invention relates to knee prostheses and more specifically to surface guided total knee replacement prostheses.

BACKGROUND OF THE INVENTION

One of the major objectives of an artificial knee joint is to restore the mechanics of the anatomic knee. However the anatomic knee is complex, consisting of structures such as the articular surfaces, ligaments, and muscles, which cannot all be replicated by artificial parts at this time. This problem is mitigated by the fact that arthritis involves destruction of the condylar bearing surfaces and the menisci, while the remaining parts of the knee are largely intact and can still function. Hence, if an artificial knee joint provides a replacement for the bearing surfaces using metal and plastic materials, reasonably normal joint function can theoretically be achieved. This is the fundamental principal behind the large majority of the resurfacing types of knee joint that have been designed since about 1970.

There have been a number of design features introduced to optimize the configurations of artificial knees. Dishing of the tibial bearing surfaces has increased the inherent stability of the artificial knee and has also reduced the contact stresses on the plastic, to increase durability. This dishing has been considered especially important in many designs, because of the requirement to resect the anterior cruciate ligament. Even when it has been present, the difficulty of the surgical technique in retaining the anterior cruciate ligament has led to a preference for resection. Surgical considerations have also led to the further step of resecting the posterior cruciate. When both the anterior and posterior cruciate ligaments are resected, the dishing of the tibial surfaces becomes even more important to provide anterior-posterior, as well as rotational, stability to the knee. When there is only a compressive force across the knee, and no shear force, the femur will locate at a "dwell point" or "bottom-of-the-dish" in the plastic tibial surface. This dwell is constant throughout the range of flexion in a standard total knee design.

A feature of normal knee motions that was seen as an advantage was posterior displacement of the femur on the tibia as flexion proceeded. This was thought to increase the lever arm of the quadriceps and to allow for a higher range of flexion. In configurations which retained the posterior cruciate ligament, this motion was achieved so long as the placement of the components allowed for the natural tightening of the posterior cruciate with flexion. But in configurations where both cruciates were resected, some other mechanism was required to obtain the posterior displacement.

The most widely used mechanism was an intercondylar cam, where a plastic post in the center of the tibial component, projected upwards into a metal housing between the metallic medial and lateral femoral condyles. In one of the first artificial knees using an intercondylar cam (Walker et al, U.S. Pat. No. 4,209,861), the housing articulated against the post throughout the entire flexion range, producing continuous rollback. In subsequent designs, the cam came into contact in the mid-range of flexion. This type of artificial knee configuration has been termed posteriorly stabilized, or PS, knees.

The large majority of the knees implanted today are of the posterior cruciate retaining (CR) or PS types. These have functioned well, but a number of disadvantages remain. Due to variations in surgical techniques, it has been difficult to obtain an optimal tightness with the CR of the posterior cruciate throughout flexion, resulting in variable rollback patterns. For the PS, considerably extra bone needs to be resected from the center of the femur to accommodate the intercondylar housing of the femoral component, there is often long-term damage to the plastic post, and there is a tendency for overconstraint in rotation due to the dishing of the tibial bearing surfaces.

A disadvantage common to both CR and PS types, although more pronounced with CR designs due to their shallower tibial bearing surfaces, is a paradoxical motion in which the femur slides forwards on the tibial surface during flexion, rather than backwards which is the required motion. Also, uneven or jerky motion occurs in many cases. These abnormalities occur because in flexion, the smaller distal-posterior sagittal radius of the femoral component comes into contact with the tibial bearing surface resulting in less constraint to anterior sliding of the femur. This dilemma was partially addressed for mobile bearing condylar knees, when femoral-tibial conformity was a particular goal, as in U.S. Pat. Nos. 5,906,643 and 6,264,679B1 to Walker wherein a solution was disclosed in which notches at the sides of the lateral and medial condyles, continuations of the distal-posterior radius, articulated with matching surfaces on the plastic tibial component. This arrangement was claimed to extend the degrees of flexion over which the condyles were in close contact. One of the main rationales for this arrangement was to provide a single anterior contact in early flexion and a progressively posterior contact in late flexion.

Another feature of anatomical knee motion, as well as a general posterior translation of the femur on the tibia, is rotation of the tibia about its long axis. There are two ways in which this rotation can occur. Firstly, as the knee flexes, there is usually a continuous internal rotation of the tibia. The axis has been found to locate on the medial side of the knee and hence the lateral femoral condyle displaces posteriorly, but the medial femoral condyle displaces only a small amount in comparison. While artificial knees have included configurations that accommodate medial pivotal rotation, these configurations lack an integral mechanism that promotes the anatomical motions of rollback in flexion, medial pivotal rotation and roll forward in extension.

The second type of rotation, termed laxity, is that at any angle of flexion, the tibia can be rotated internally and externally with respect to the neutral position. The amount of rotation towards extension is about 10 degrees on either side of neutral, but this increases to about 20 degrees on either side of neutral by about 30 degrees flexion. In high flexion the laxity apparently reduces again, but there is little quantitative data available. In condylar replacement artificial knees, laxity occurs due to the partial conformity between the femoral and tibial bearing surfaces. The shallower are the tibial surfaces, the greater the laxity. Towards extension, there is closer conformity and less laxity, compared with the laxity in flexion. In a general way, this laxity reproduces the situation in an anatomic knee joint. While partial conformity in an artificial knee is desirable in providing laxity, the contact point tends to be located at the 'bottom of the dish' such that it does not displace anteriorly and posteriorly in extension and flexion, nor does it rotate internally with flexion.

An ideal artificial knee configuration would be one where the neutral path of motion, and the laxity about that neutral path, was similar to that of the anatomic knee. In this way, the motion would be compatible with the surrounding soft tissue envelope and the musculature of the knee. In our configuration, the femoral and tibial bearing surfaces are constructed to replace the mechanical function of the anatomic cartilage surfaces, the menisci, and the cruciate ligaments. A surface design with smooth transitions of curvatures has the advantages that large contact areas can be maintained, the motion will be smooth, and there is no possibility of damage to cams or other projections. In fact, in extreme motion conditions or if the artificial joint has been installed so that it is too loose in flexion, actual dislocation over a cam post can occur. For a surface configuration with no cam or projections, this could not occur.

The subject of this invention is a surface design of an artificial knee with continuous curvatures whereby posterior displacement occurs automatically with flexion, with the effect that the dwell point moves progressively posterior with flexion, as in the anatomic knee. Conversely, as the knee is extended from a flexed position, the dwell point moves anteriorly. To more closely replicate the neutral path of motion of the anatomic knee. The surfaces can be designed or configured so that the neutral path in flexion involves internal rotation of the tibia, and conversely as the knee is extended again. Finally the surfaces can also be made to minimize paradoxical motion in early flexion. In all these schemes, the surfaces are such that rotational laxity is possible about the neutral path as in the anatomic knee.

SUMMARY OF THE INVENTION

A number of characteristics which are ideally included in the configuration are as follows. The posterior displacement is small from approximately 0-45 degrees flexion, which has the advantage that a large area of contact can be maintained in that major functional range. The total posterior translation should be approximately 10-15 mm, but where the posterior limit is not too close to the posterior edge of the tibial component. The reason is that some rotational laxity is still needed in high flexion and it is undesirable if the femoral condyles ride on or over the very posterior edge of the tibial component. The patella mechanism is an important consideration in an artificial knee.

In the anatomic knee, past about 110 degrees flexion, the contact between the patella and the digital end of the femur splits into two separate areas on the lateral and medial condyles. Most artificial knees cause the same scheme, especially when intercondylar cams are used. However, it would be an advantage is contact in high flexion was over the entire width of the patella, which would considerably reduce the stresses on the artificial patella and the remaining bone. Continuous contact is possible with a surface guided design or configuration.

BRIEF DESCRIPTION OF THE DRAWINGS

Preferred embodiments of the invention are described below with reference to the drawings, wherein like numerals are used to refer to the same or similar elements.

DETAILED DESCRIPTION OF PREFERRED EMBODIMENTS

Figure 1A:
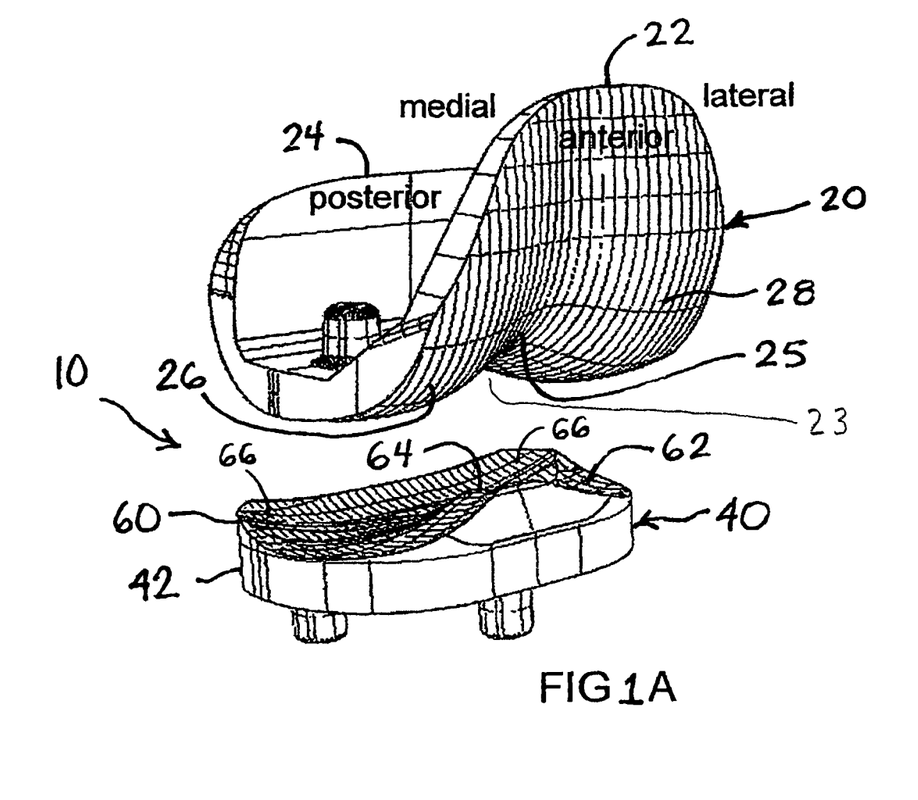
FIG. 1A is an anterior-medial isometric view of a typical femoral component and tibial component showing the anterior position of the patella flange of the femoral component.

Referring to FIG. 1A, a surface guided knee replacement 10 is shown in a position of approximately zero degrees flexion and includes a femoral component 20 and a tibial component 40. Femoral component 20 connects to a shaped distal end of a femur. In the embodiment shown, the tibial component 40 is one-piece, but can also be a bearing component fixed into a tibial tray or baseplate. The tibial component 40 connects to a shaped proximal end of a tibia and includes a bearing surface 62 that receives and guides the flexion of femoral component 20.

Femoral component 20 has a proximal-anterior portion 22 and an opposed proximal-posterior portion 24 that define an arcuate curve. Component 20 includes an intercondylar surface 25 that connects a medial condyle 26 and a lateral condyle 28. Intercondylar surface or patella groove 25 defines a recess or notch that has a depth that progressively diminishes from the proximal-anterior portion 22 to the proximal-posterior portion 24. Condyles 26 and 28 have convex outer surfaces. The portions of condyles 26 and 28 that interface with tibial bearing surface 62 have radii that decrease along the arcuate curve in the direction from the proximal-anterior portion 22 to the proximal-posterior portion 24.

Figure 1B:
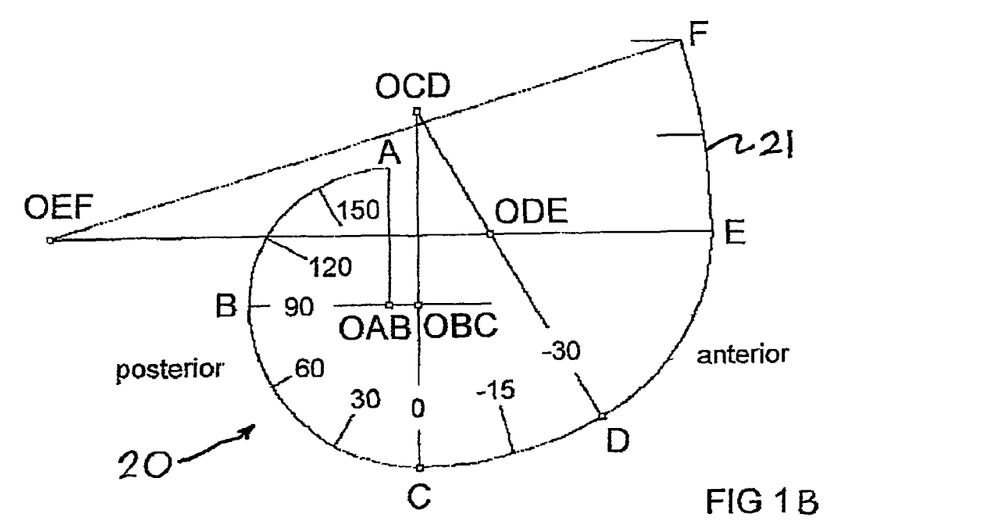
FIG. 1B is a side cross-sectional sagittal plane view of an outer surface of a femoral component that has sections from −30 to 150 degrees constructed in accordance with the present disclosure.
Figure 1C:
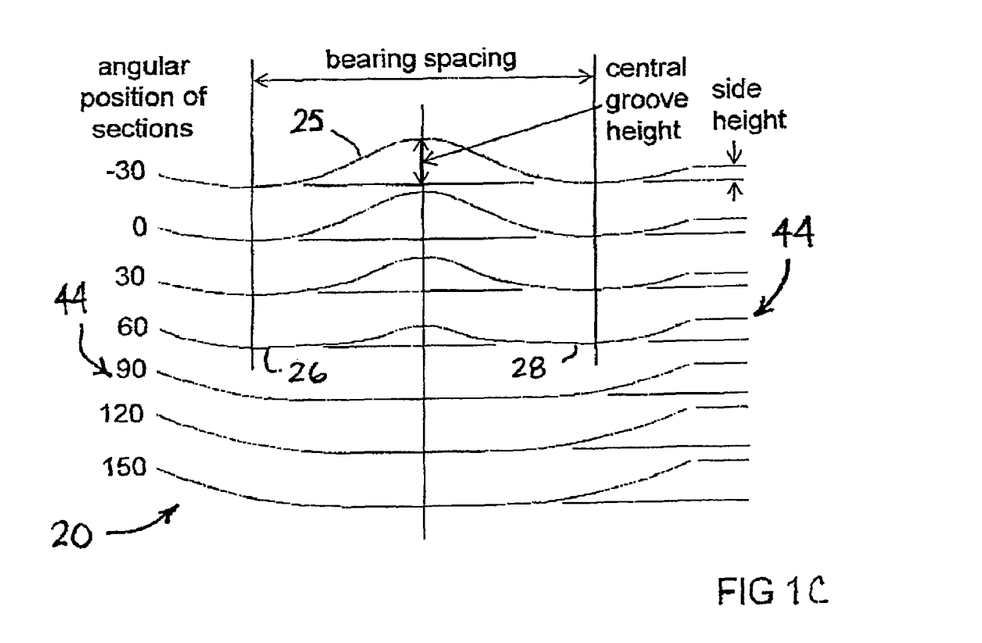
FIG. 1C is a series of partial cross-sectional frontal views of the surface of each of the sections of the femoral surface of FIG. 1A at different flexion angles from −30 to 150 degrees.

As shown in FIGS. 1B-1C, the outermost section of femoral component 20 has a sagittal profile 21 that is composed of five separate arcs joined tangentially. Sagittal profile 21 includes arc AB, with center OAB, arc BC with center OBC, arc CD with center OCD, arc DE with center ODE and arc EF with center OEF. Arcs AB, BC and CD extend from greater than 150 degrees to −30 degrees. Proximal-anterior portion 22 of profile 21 includes point A and proximal-posterior portion 24 includes point F. In profile 21, arc AB or the posterior-distal portion of femoral condyles 26 and 28, retains contact with bearing surface 62 of tibia 40 in high flexion to avoid bony impingement.

In flexion from about zero degrees at point C through approximately 90 degrees flexion at point B, a constant femoral radius of arc BC contacts receiving surface 62 and advantageously assists in maintaining the same arcuate profile in contact with receiving surface 62. From 60 to 90 degrees flexion the constant radius of femoral component 20 is maintained to achieve the desired height requirement that arc AC is taller than that in the anatomic knee. The radii from points C to F are chosen to be a close match to the anatomic knee and give the desired shape of the patella trochlea and the average anterior-posterior dimension of femoral component 20. Condyles 26 and 28 can have the same radii and arc profiles 21, but different shapes can also be used. In an anatomic femur, the profiles of the lateral and medial condyles are different.

Continuing with FIGS. 1B-1C, the location of the frontal plane sections of profile 21 are shown in FIG. 1C, designated by their angular position along their respective arcs. From 0-150 degrees, there is a correspondence with the angle of flexion of the knee. FIG. 1C shows the shape of these sections seen in frontal views of the femoral component 20 at the corresponding flexion angle. From −30 to 0 degrees flexion, the sections are approximately anatomic including the central height and shape of the patella groove 25, bearing spacing (distance between the high points on the lateral condyle and medial condyle) and frontal radii which is reflected in a side height 44. From 0-90 degrees flexion there is a progressive reduction in the central height of the patella groove that reaches zero at approximately 90 degrees flexion.

In the anatomic knee, the patella contacts the distal region of the femur on the 0-30 degrees section when the knee is flexed maximally at about 150 degrees. Hence the shape and depth of the anatomic knee are essentially maintained for this purpose. It will later be shown that the reducing height of the grooved intercondylar surface 25 with flexion will create a ramp 64 on tibial receiving surface 62 of similarly diminishing height and width.

After 30 degrees flexion, the side height 75 of the sections of the tibial surface 62 steadily increases. The increased side height 75 supports the posterior displacement of femoral component 20 during flexion, preserves bearing surface 62 for stability in early flexion and creates ramps 66 at the postero-lateral and postero-medial corners of the tibial component that promotes roll forward as the knee is extended from maximum flexion. In the sections from 90-150 degrees, the side curvature begins closer to the center than the bearing spacing. This increases the thickness of the ramp mentioned above and further promotes roll forward.

Femoral component 20 and tibial component 40 are preferably made of metal and a polymer material, respectively. The interface between femoral component 20 and receiving surface 62 is intended to provide the extended wear characteristics that are desirable in a knee replacement.

Figures 2A, 2B, 2C:
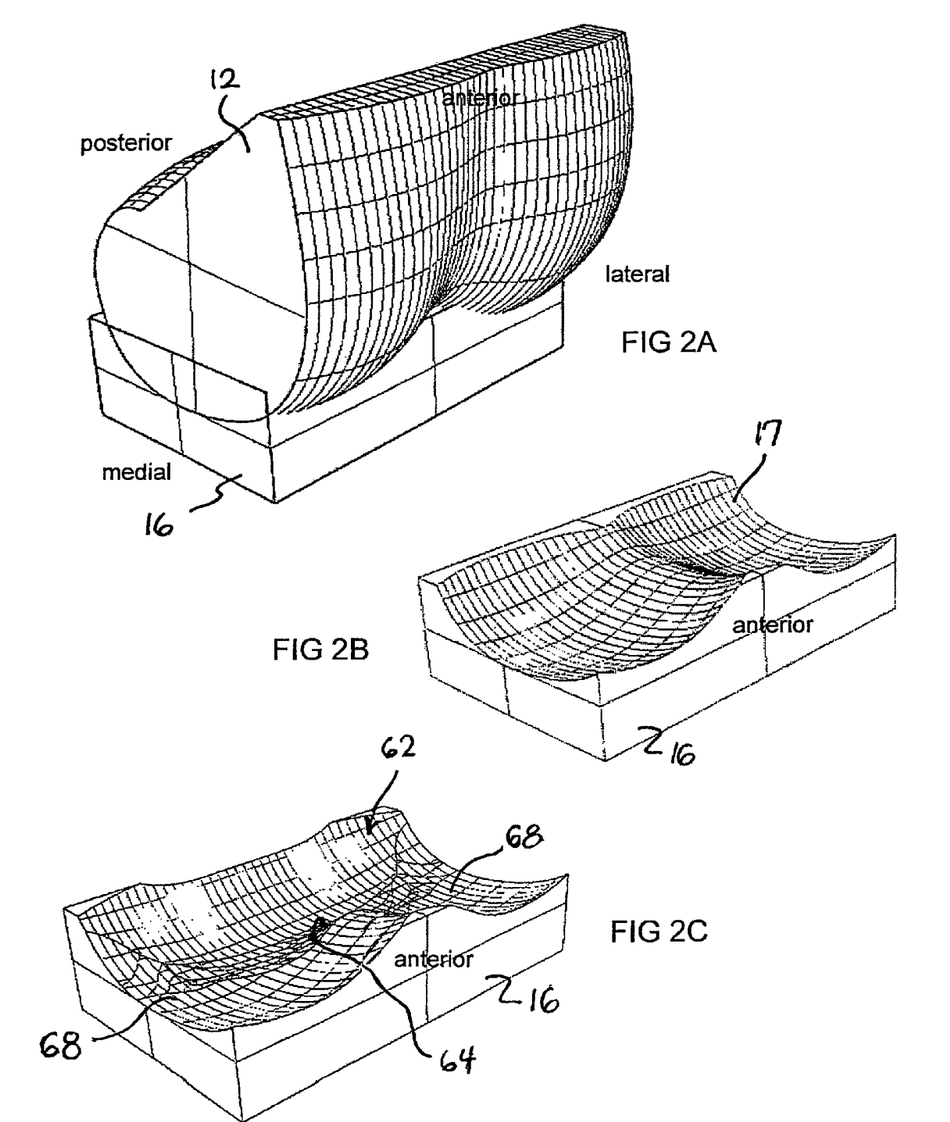
FIG. 2A is the generating femoral block of FIG. 1A seated inside a solid rectangular tibial block at zero degrees flexion.
FIG. 2B is the tibial block of FIG. 2A after a Boolean subtraction has been performed for the imprint of the generating femoral block at a position of approximately zero degrees flexion.
FIG. 2C is one embodiment of the tibial block of FIG. 2A showing facets after the generating femoral block has been placed in a limited number of successive positions through the flexion range and an overall tibial surface is produced.
Figure 3A:
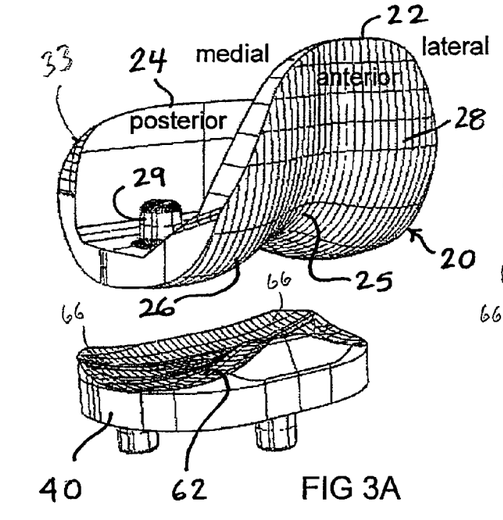
FIG. 3A is an antero-medial perspective exploded view of a surface guided knee replacement that has a femoral component and a tibial component constructed in accordance with the present disclosure.
Figure 3B:
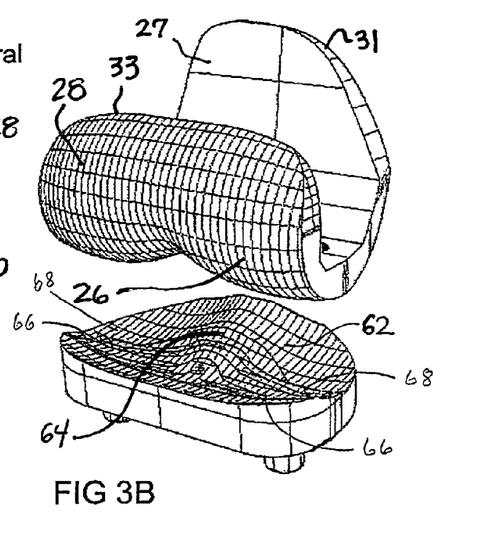
FIG. 3B is a postero-medial perspective exploded view of the knee replacement of FIG. 3A.
Figures 3C, 3D:
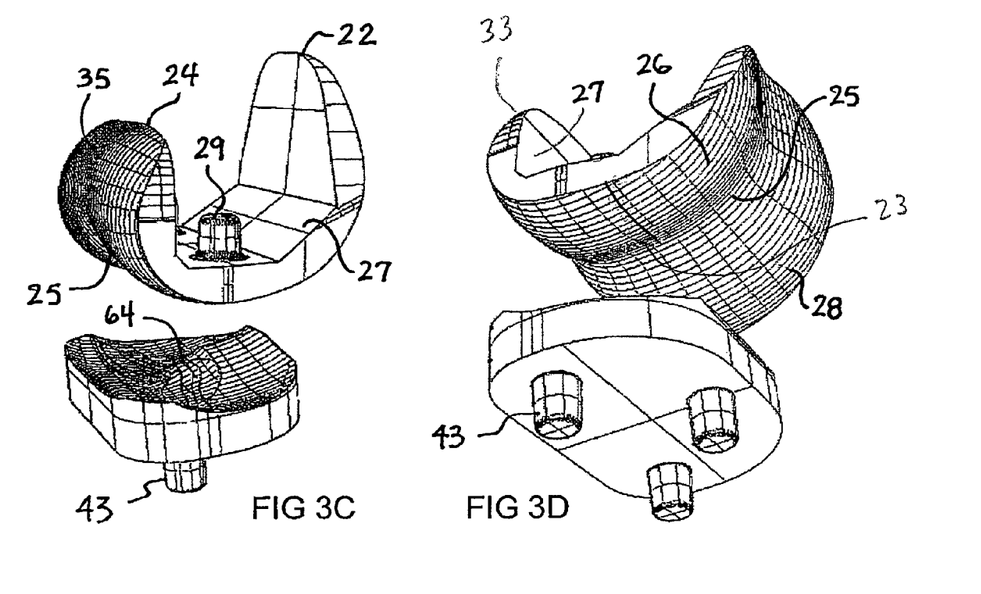
FIG. 3C is a postero-medial perspective exploded view of the knee replacement of FIG. 3A showing an anterior to posterior descending ramp in the center of the tibia.
FIG. 3D is a bottom perspective exploded view of the knee replacement of FIG. 3A showing the patella groove.

As shown in FIGS. 2A and 2B, the generating solid femoral block 12 is three-dimensionally shaped into the sections of FIG. 1C along the longitudinal axis between the approximately −30 degrees to approximately 150 degrees of flexion as shown in FIG. 1B. Generating femoral block 12 can be exactly the same or have an approximately similar shape and dimension as that of femoral component 20. Femoral block 12 is seated into a tibial block 16, to a depth of seating of approximately 10 mm that provides sufficient dishing of the final tibial component. Femoral block 12 is at zero degrees flexion. Using a Boolean subtraction process that is common to present 3-D modeling software packages, the generating femoral block 12 is subtracted from the tibial block 16. This initial process produces a smooth tibial receiving surface 17.

The generating femoral block 12 is then restored and adjusted in position. This adjustment of position includes a flexion of the generating block about a defined axis, a posterior translation, and a small downwards translation that simulates the movements of the actual knee joint. A table is made of these movements. In our example, the defined axis of rotation was OBC for 0-90 degrees flexion and OAB for 90-150 degrees flexion. The posterior translation was approximately zero from a range of approximately 0 degrees to as much as approximately 50 to 60 degrees flexion. From as early in flexion as 50 degrees, the translation is preferably increased in steps to 12 mm until approximately 150 degrees with a range of translation from approximately 10-15 mm being acceptable. The downward translation paralleled the five degrees posterior slope of the tibia. Other patterns of motion than the above could be used so long as the essential posterior translation was included.

Referring now FIG. 2C, generating femoral block 12 is placed on the tibial block 16 in increments of flexion that correspond to angles of flexion and Boolean subtractions are then performed at each angle. This produces a tibial surface 62 that includes two laterally opposed condyle receiving areas 68 separated by an anterior to posterior descending ramp 64. Ramp 64 descends, in an anterior to posterior direction, relative to said two laterally opposed condyle receiving areas, and blends into said tibial surface before reaching a posterior edge of said tibial component. The individual facets reflect the interface between the femoral block 12 and tibial block 16 for each of the increments of flexion. To produce a smooth surface, steps at small angular increments, and/or smoothing in software, can be carried out.

When the generating femoral block 12 is placed on the tibial bearing surface 17, from zero to 50 degrees, there is a large area of contact between the full width of femoral block 12 and tibial bearing surface 62. This provides stability in the anterior-posterior direction but also prevents more than a few degrees of internal-external rotation. In order to allow for more rotational laxity in early flexion, the generating femoral block 12 can be expanded by a small percentage in the anterior-posterior direction, which opens out the condyle receiving areas 68 positioned on the opposing lateral sides of ramp 64 on tibial surface 62. After 50 degrees flexion, it is found that there is adequate internal-external rotation possible.

Referring now to FIGS. 2A and 3A-3D, starting from generating femoral block 12 and tibial block 16, femoral component 20 and the tibial component 40 are generated. In this one preferred embodiment, the distal end of the femur is cut with one standard method of shaping that includes five facets that mate with the five planar inwardly facing sides 27 of femoral component 20. It is understood that the inwardly facing sides 27 that oppose the outwardly positioned convex condyles 26 and 28 can have any shape. For added fixation to the femur, femoral component 20 can also include two or more short pegs 29, although many other fixation means are possible.

Towards the proximal-anterior portion or end portion 22, component 20 converges inwardly 31, especially on the medial side. At the proximal-anterior portion 22 of femur component 20, the edges 31 of the patella flange are rounded. The proximal-posterior portion 24 also has rounded edges 33 to conform with the shape of the femur. Rounded edges 31 and 33 advantageously provide smooth sliding of soft tissues including muscle, tendon and capsular tissue, over the edges of the femoral component 20.

Overall, the contour of femoral component 20 is shaped and dimensioned to be a close match to that of the anatomic femur, except that the height of the posterior portion of condyles 26 and 28 is preferably approximately 2 mm higher to avoid impingement of the posterior femoral condyles with the posterior edge of the tibial component 40, in high flexion. On the anterior of femoral component 20, the patella groove 25 is anatomic in profile. This profile carries round to the proximal-anterior portion 22 where the patella contacts in high flexion. From the proximal-anterior portion 22 to region 27 or at approximately 110 degrees flexion, the depth of patella groove 25 resembles the anatomic. Posterior to the region 27, the depth of groove 25 steadily diminishes until it reaches zero in proximity to region 35 in the vicinity of proximal-posterior portion 24. In the posterior region of the femoral component 20, the central region of the surfaces can be close to cylindrical.

The bottom of tibial component 40 is shaped to fit the resected surface of the upper tibia. Tibial component 40 preferably uses three fixation pegs 43, although many other fixation means are possible. In another embodiment, tibial component 40 can be mounted on a metal baseplate which is fixed to the upper tibia, such that the tibial component 40 can rotate on the surface of the baseplate.

As shown in FIGS. 1C and 4A-4C, femoral component 20 is shown in contact with receiving surface 62 of tibial component 40 through a range of motion from approximately zero degrees flexion to approximately 120 degrees of flexion. The area of contact between femoral component 20 and tibial component 40 moves posteriorly from the approximately zero degree position of flexion to the approximately 60 degree and approximately 120 degree positions during flexion.

Side height 34 is preferably approximately 2-3 mm between 0 degrees to about 50 degrees flexion. Thereafter, the side height increases at a preferably steady rate to approximately 6-8 mm in the higher ranges of flexion from approximately 50 to 150 degrees in the proximal-posterior portion or end portion 24 of femoral component 20.

This arrangement produces elevated ramps 66 (FIGS. 3A and 3B) in the postero-lateral and postero-medial corners of the tibial surface 62. When the knee is extended from a fully flexed position, these ramps facilitate rolling of the femoral component 20 in an anterior direction. When the femoral component 20 is nearing extension, it now seats in the lower regions of condyle receiving surfaces 68 on tibial surface 62. At approximately 120 degrees flexion and beyond, the contact is approximately 10 mm from the posterior of tibial component 40.

Figures 4A, 4B, 4C:
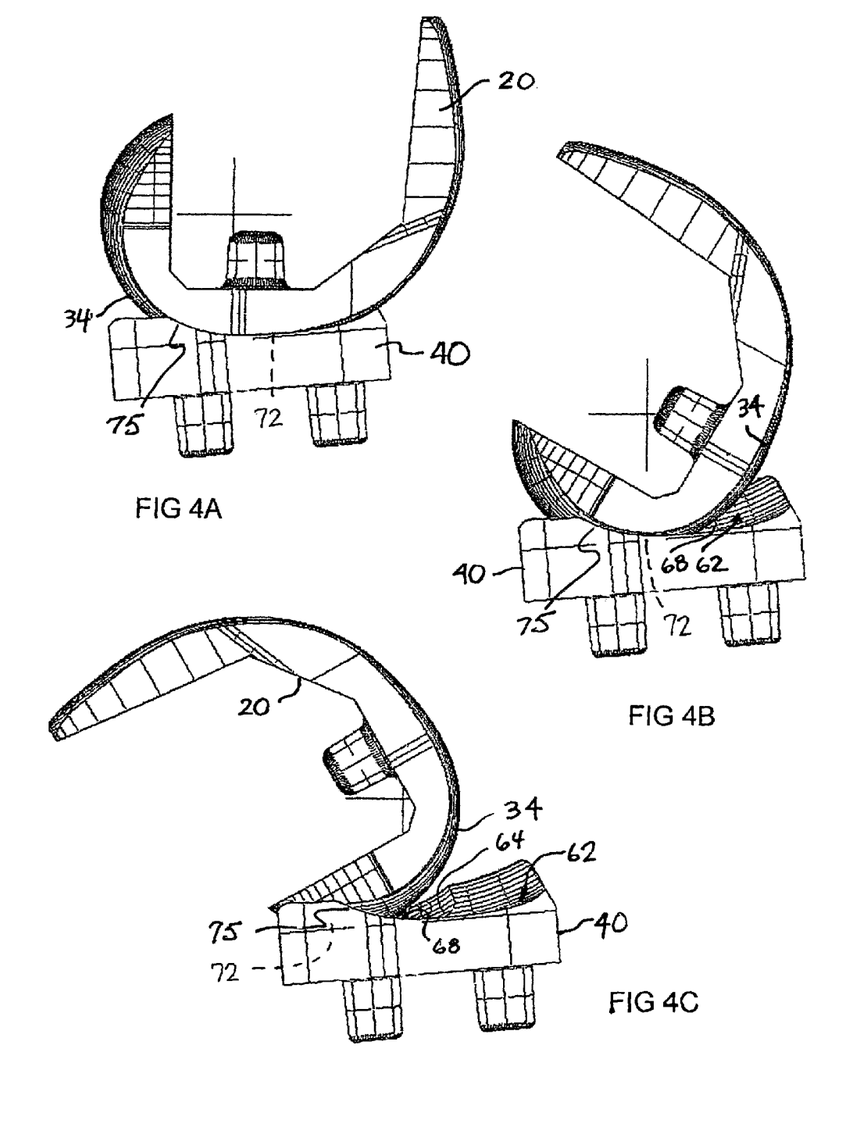
FIG. 4A is a side view of the knee replacement of FIG. 3A with the tibial component positioned at a five degrees posterior slope and the femoral component at a position of approximately zero degrees flexion.
FIG. 4B is a side view of the knee replacement of FIG. 4A at a position of approximately 60 degrees flexion.
FIG. 4C is a side view of the knee replacement of FIG. 4A at a position of approximately 120 degrees flexion.
Figures 5A, 5B, 5C, 5D:
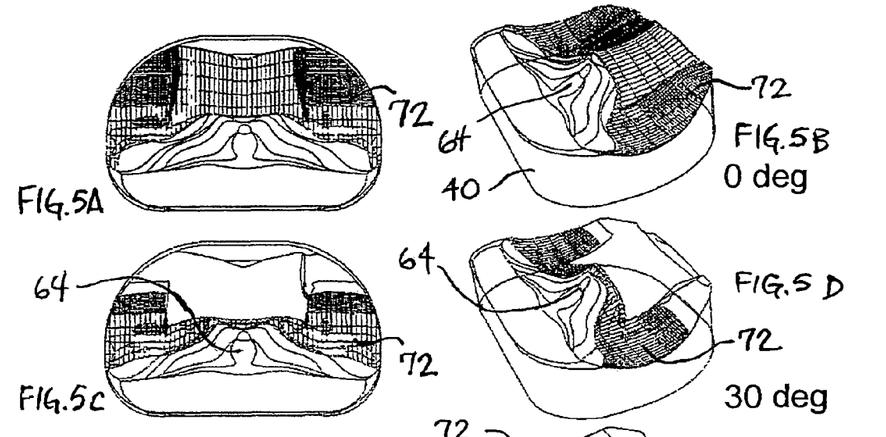
FIGS. 5A-5L show the movement of the contact areas of the femoral component on the tibial bearing surface of the knee replacement of FIG. 4A from the approximate zero degrees flexion through the approximate maximum flexion.
Figure 5E:
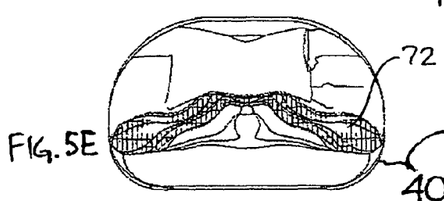
Figure 5F:
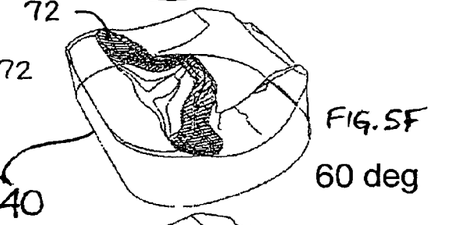
Figure 5G:
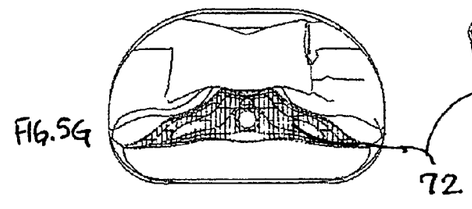
Figure 5H:
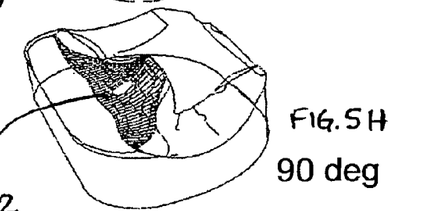
Figure 5I:
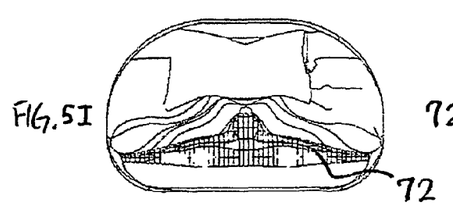
Figure 5J:
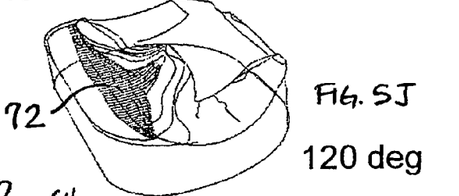
Figure 5K:
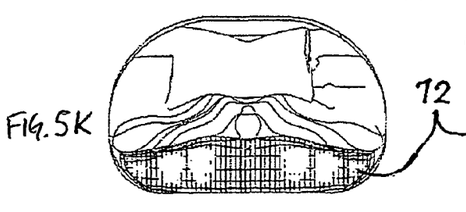
Figure 5L:
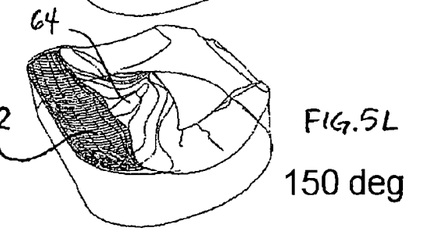

As shown in FIGS. 4A and 5A-5B contact area 72, shown as the darkened area of the anterior of bearing surface 62 defines the interface between femoral component 20 and tibial component 40 at zero degrees flexion. The large contact area 72 shows the close conformity between components 20 and 40 at approximately zero degrees flexion. Contact area 72 covers from the anterior to just behind the center of tibial receiving surface 62. The center of pressure will depend on the prevailing joint force. If there is an extending moment on the femur, the center of pressure will tend to lie at the anterior, acting as a brake to further extension.

Referring now to FIGS. 4B, 5B-5D as flexion increases, contact area 72 moves progressively posteriorly, as indicated by the arcuate lines which pass across the component in a medial-lateral direction. At 30 degrees flexion the contact moves to the posterior part of the anterior contact region, due to the arc BC (FIG. 1B) being in contact. In particular, patella groove 25 receives central ramp 64 on bearing surface 62. Ramp 64 has a height that decreases from the anterior to the posterior of tibial component 40 and sides that are concave slopes. The height and slope of the sides of ramp 64 guide femoral component 20 to displace posteriorly during flexion and displace anteriorly during extension.

Up to approximately 50 degrees flexion, contact area 72 does not move further posterior than shown contact regions 72. At approximately 60 degrees flexion, contact area 72 transitions to a band across the tibial surface just to the posterior to the center of tibial receiving surface 62.

As shown in FIGS. 4C and 5E-5L, from approximately 60 degrees flexion to 90, 120, and 150 degrees flexion, contact area 72 remains as a lateral band across the tibial surface that moves progressively more posterior with flexion. At each angular position of flexion, there is both anterior and posterior stability of femoral component 20 on the tibial receiving surface 62 due to the different discrete slopes across the tibial surface.

Figure 6A:
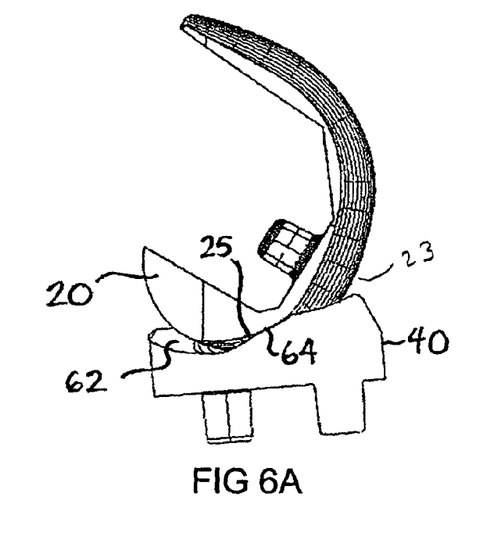
FIG. 6A-6C are mid-sagittal cross-sectional views of the knee replacement of FIG. 3A at 60, 90 and 120 degrees flexion showing the lowest contour of the femoral intercondylar region for each respective angle of flexion that contacts the ramp of the tibial component.
Figure 6B:
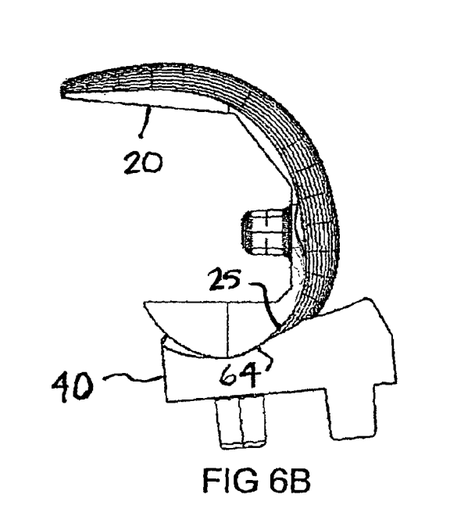
Figure 6C:
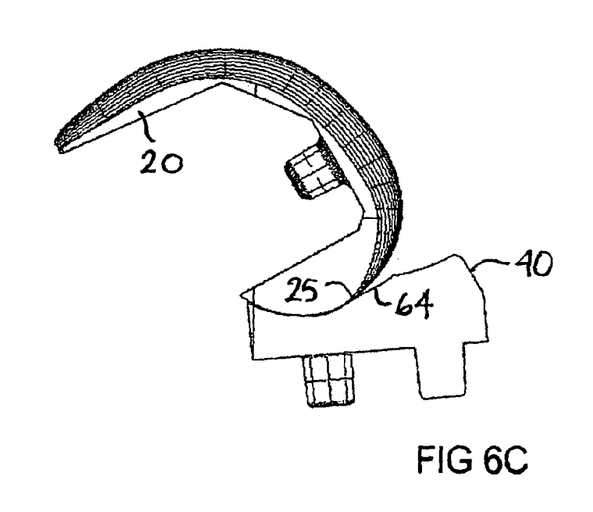

Referring now to FIGS. 6A-6C, are sagittal sections through the center of femoral component 20 and tibial component 40 and show the interaction of patella groove 25 between the base of patella grove 25 at approximately 60 degrees flexion and the posterior extension of patella groove 25 with ramp 64 in the center of the tibial receiving surface 62 at approximately 120 degrees flexion. In this one preferred embodiment, groove 25 initially makes contact with ramp 64 between approximately 30-60 degrees flexion. As femoral component 20 flexes to 90 degrees (FIG. 6B), contact has moved down ramp 64 and ramp 64 has effectively displaced the femoral component 20 posteriorly. On further flexion to 120 degrees (FIG. 6C), the extension of the patella groove 25 has reached the bottom of the ramp 64.

At 120 degrees flexion and beyond, the contact area of f the femoral component 20 on the tibial receiving surface 62 is preferably at least 8 mm and as much as approximately 10-12 mm from the posterior of the tibial component 40 and receiving surface 62 is shaped to maintain femoral component 20 at this position up to maximum flexion. As noted above, this is an advantage because internal-external rotation of the femur on the tibia is possible without the femur contacting the extreme posterior edge of tibial component 40.

Figure 7A:
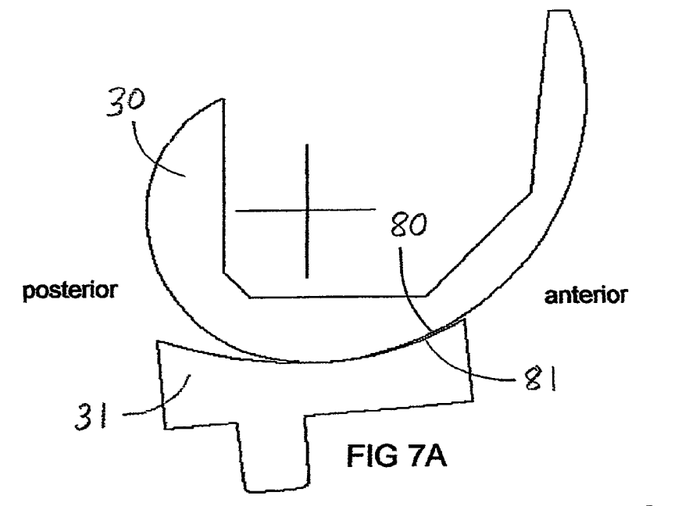
FIG. 7A is a mid-condylar sagittal plane cross-sectional view of a simplified replacement knee at approximately zero degrees flexion showing the closely matching interface of the femoral anterior curvature with the tibial anterior curvature and their respective radii.

As shown in FIG. 7A, a simplified replacement knee is positioned at zero degrees flexion where there is a close conformity between the anterior curves of the femoral component 20 and tibial receiving surface 62. If there is a shear force applied that would move the femoral component 20 anterior relative to the tibial component 40, there will only be a small relative displacement because of the close conformity.

Figure 7B:
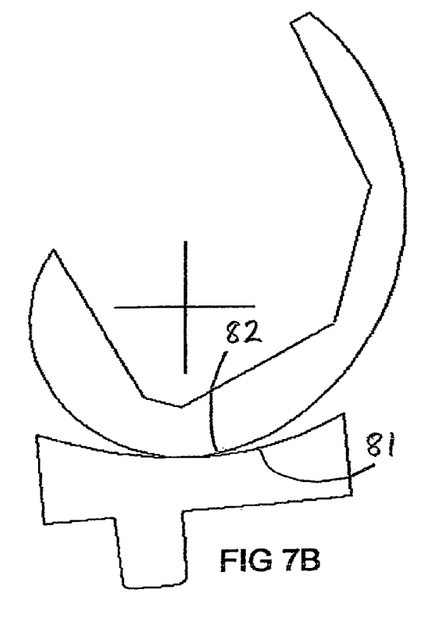
FIG. 7B is a simplified mid-condylar sagittal plane cross-sectional view of the replacement knee of FIG. 7A at approximately 60 degrees flexion with the contact point in the central region of the tibial curvature.
Figure 7C:
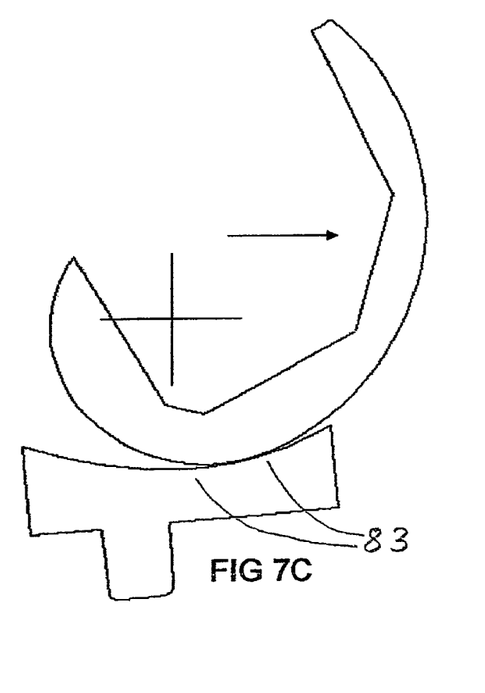
FIG. 7C is a simplified mid-condylar sagittal plane cross-sectional view of the replacement knee of FIG. 7A at approximately 60 degrees flexion that shows anterior sliding of the femoral component on the tibial component.

Referring now to FIGS. 7B and 7C, when the replacement knee is flexed, the reduction in the radius of condyles 26 and 28 can cause a loss of contact area and conformity between femoral component 20 and tibial receiving surfaces 62. If an anteriorly directed shear force is applied as shown by arrow A in FIG. 7C, there will be an anterior displacement of femoral component 20 on tibial receiving surface 62. This has been termed paradoxical motion and does not resemble normal anatomic motion in which the femur displaces posteriorly with flexion. Such paradoxical motion is not desirable in an artificial knee because it reduces the lever arm of the quadriceps muscle, and can impair the ability to climb stairs and reduce the range of flexion.

Figures 8A, 8B, 8C, 8D, 8E:
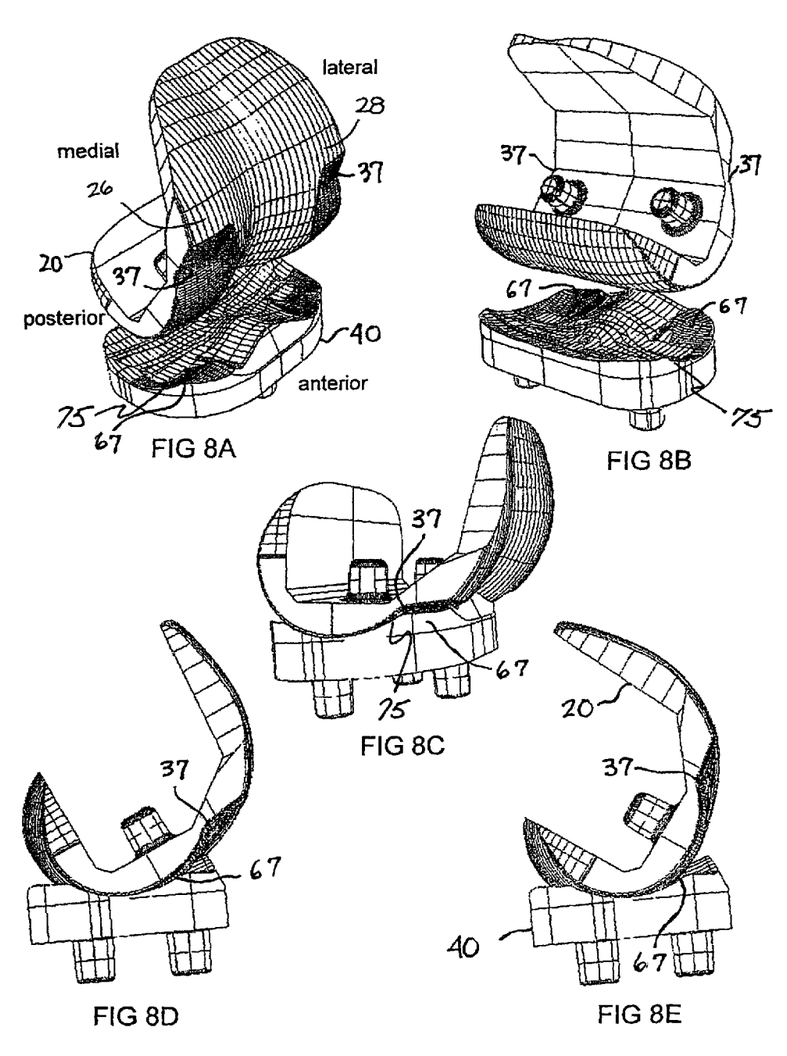
FIG. 8A is an antero-medial plan perspective exploded view of the surface guided knee replacement of FIG. 4A that shows notches positioned on the side of the femoral component and corresponding pads on the tibial component.
FIG. 8B is a postero-medial plan perspective exploded view of the surface guided knee replacement of FIG. 8A.
FIG. 8C is an antero-medial plan perspective view of the surface guided knee replacement of FIG. 8A with the femur component at the zero degree flexion position on the tibial component.
FIG. 8D is a side view of the surface guided knee replacement of FIG. 8A with the femur component at the 30 degree flexion position on the tibial component.
FIG. 8E is a side view of the surface guided knee replacement of FIG. 8A with the femur component at the 60 degree flexion position on the tibial component.

One of the methods for avoiding paradoxical motion is shown in FIG. 8A-8E. Notches 37 are cut in the sides of medial condyle 26 and lateral condyle 28 of femoral component 20. Notches 37 articulate against corresponding pads 67 in proximity to the anterior outside edges of tibial component 40. As best seen in FIG. 8C, notch 37 in femoral component 20 has the same radius R as the distal-posterior radius of the lateral 28 and medial 26 femoral condyles. When femoral component 20 is flexed to approximately 30 degrees (FIG. 8D) or 60 degrees (FIG. 8E), the notches 37 mate with the pads 67, and prevents anterior translation of femoral component 20 on tibial component 40. Or in other words, the interaction of the pads and notches prevents the femoral component from skidding forward on the tibial component during early flexion. Therefore, when the knee is close to extension, as shown in FIG. 8C, for example, there is a small gap or space between the upper shelf of notch 37 on the femoral component 20 and the top of pad 67 on tibial component 40 in order to allow a few degrees of hyperextension.

It is an advantage if the edge of the notches 37 and pads 67 are rounded to avoid catching if the alignment of the knee is not exactly central as the knee is extended. The width of the notches 37 on the femoral component 20 are such that they do not interfere with the region that the patella traverses. In this regard, the medial notch can be wider than the lateral, because the patella bearing area is more extensive on the lateral side.

In the preceding specification, the invention has been described with reference to specific exemplary embodiments thereof. It will be evident, however, that various modifications, combinations and changes may be made thereto without departing from the broader spirit and scope of the invention as set forth in the claims that follow. It is understood that the present invention can combine one or more novel features of the different embodiments. The specification and drawings are accordingly to be regarded in an illustrative manner rather than a restrictive sense.

What is claimed is:

1. A knee prosthesis comprising:
   a tibial component comprising a tibial surface that includes two laterally opposed condyle receiving areas separated by a center ramp that descends, in an anterior to posterior direction, relative to said two laterally opposed condyle receiving areas, and blends into said tibial surface, said center ramp having concave sloped sidewalls, said tibial surface further comprising a first elevated ramp located at the postero-lateral corner of said tibial surface and forming a lateral edge that defines a lateral tibial side height and a second elevated ramp located at postero-medial corner of said tibial surface and forming a medial edge that defines a medial tibial side height, wherein said lateral and medial tibial side heights increase in the anterior to posterior direction; and
   a femoral component comprising condylar outer surfaces, in articulating contact with said condyle receiving areas, that have sagittal profile radii that decrease along an arcuate curve in a direction from a proximal-anterior portion of said femoral component to a proximal-posterior portion of said femoral component, wherein profiles of frontal plane sections comprise frontal radii that form lower portions of said condylar outer surfaces, said frontal radii define femoral side heights that increase with increases in flexure angle of said femoral component.

2. A knee prosthesis in accordance with claim 1 wherein said femoral component further comprises:
   a groove that extends from a vicinity of a proximal-anterior region of said femoral component to a vicinity of a proximal-posterior region of said femoral component, said groove diminishes in depth from the distal region of said femoral component to the proximal-posterior region of said femoral component; and
   a portion of the surface of said anterior to posterior descending ramp is positioned to contact a portion of the surface of said groove and operatively configured to induce posterior displacement of said femoral component in response to flexion.

3. A knee prosthesis in accordance with claim 2 wherein the depth of the groove at the distal end of the femoral component is greater than a depth of a natural patella groove.

4. A knee prosthesis in accordance with claim 2 wherein said posterior displacement of said femoral component on said tibial component for flexion over the approximate range of zero degrees to 150 degrees is approximately 8-14 mm.

5. A knee prosthesis in accordance with claim 1 wherein said condyle receiving areas and said condylar outer surfaces are operatively configured to provide internal-external rotational laxity.

6. A knee prosthesis in accordance with claim 1 wherein the tibial component is mounted on a baseplate and configured so that the said tibial component can rotate on a surface of said baseplate.

7. A knee prosthesis in accordance with claim 1 further comprising:
   a first notch located on distal-anterior region of a medial condyle of said femoral component and a corresponding first pad positioned at the anterior surface of said tibial component;
   a second notch located on distal-anterior region of a lateral condyle of said femoral component and a corresponding second pad positioned at the anterior surface of said tibial component;
   wherein said first and second notches and said corresponding pads are operatively configured to prevent said femoral component from skidding forward on said tibial component during early flexion.

8. A knee prosthesis in accordance with claim 7 wherein said first notch and said second notch are blended with surrounding surfaces.

9. A knee prosthesis in accordance with claim 7 wherein said first and second notches and said corresponding first and second pads have rounded edges.

10. A knee prosthesis in accordance with claim 1 wherein said femoral component has a sagittal profile that approximates the anatomical knee.

11. A knee prosthesis in accordance with claim 1, wherein said medial and lateral tibial side heights steadily increase for flexion angles greater than approximately thirty degrees.

12. A knee prosthesis in accordance with claim 1, wherein said increase in said femoral side height is approximately 8-11 mm from distal to posterior of said femoral component.

* * * * *